United States Patent

Cais

[11] 4,230,664
[45] Oct. 28, 1980

[54] TEST PACK KIT FOR IMMUNOASSAY
[75] Inventor: Michael Cais, Haifa, Israel
[73] Assignee: Technion Research & Development Foundation Ltd., Technion City, Israel
[21] Appl. No.: 5,754
[22] Filed: Jan. 23, 1979

Related U.S. Application Data
[63] Continuation-in-part of Ser. No. 795,457, May 10, 1977.
[51] Int. Cl.² .............................................. G01N 33/16
[52] U.S. Cl. .................................... 422/61; 23/230 B; 23/915; 424/12
[58] Field of Search ......................... 422/61; 23/230 B; 424/12

[56] References Cited
U.S. PATENT DOCUMENTS

| | | | |
|---|---|---|---|
| 3,272,319 | 9/1966 | Brewer | 422/61 X |
| 3,733,179 | 5/1973 | Guehler | 23/230 B |
| 3,888,629 | 6/1975 | Bagshawe | 422/61 X |
| 3,899,298 | 8/1975 | Szczesniak | 23/230 B X |
| 3,966,556 | 6/1976 | Rubenstein | 424/12 X |
| 4,022,876 | 5/1977 | Anbar | 424/12 X |
| 4,036,823 | 7/1977 | Soares | 424/12 X |
| 4,067,959 | 1/1978 | Bolz | 23/230 B |
| 4,157,323 | 6/1979 | Yen | 422/68 X |

OTHER PUBLICATIONS
Chemical Abstracts, 75:61339n, (1971).
"Hackh's Chemical Dictionary," Fourth Edition, Julius Grant, Ed., p. 264, McGraw-Hill, New York, 1969.

Primary Examiner—Sidney Marantz
Attorney, Agent, or Firm—Beveridge, DeGrandi, Kline & Lunsford

[57] ABSTRACT

A test pack kit for assaying for a ligand in a liquid medium. The kit comprises specially designed assay tubes, each tube having a cylindrical side arm which can be interconnected with the side arm of another assay tube. In addition, the pack kit contains antiserum; a conjugate of a metal labelling substance with the ligand; assay calibration standards—in vials containing known concentrations of unlabelled ligand; a separation agent in vials containing material used for separating the bound antibody—metal labelling complex from the unbound metal labelling substance and instrument calibration standards—in vials containing several known concentrations of the metal—labelling substance. Errors caused by pipetting or transferring of reagents from one container to another are practically eliminated.

14 Claims, 1 Drawing Figure

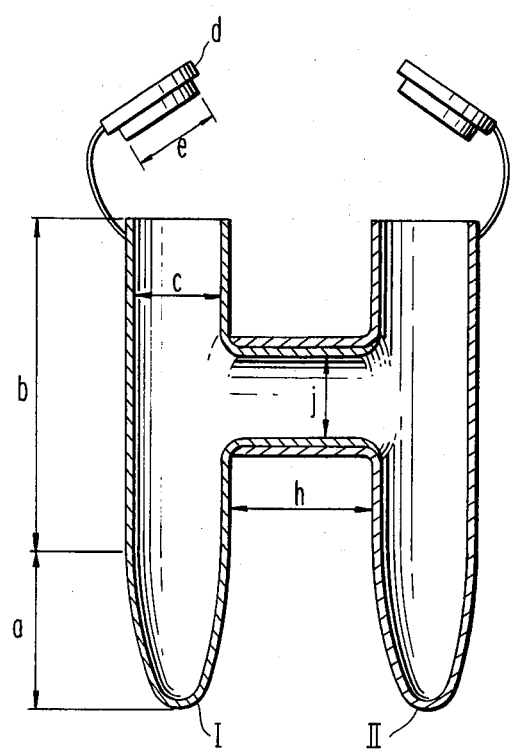

TEST PACK KIT FOR IMMUNOASSAY

REFERENCE TO A RELATED APPLICATION

This application is a continuation-in-part of co-pending application Ser. No. 795,457, filed May 10, 1977.

INTRODUCTION OF THE INVENTION

The present invention relates to a test pack kit to be used for the determination of the presence of small quantities of chemical compounds. More specifically the invention relates to a test pack kit to be used for an accurate efficient and specific analysis of small quantities of chemical compounds in man, animals and plants by a specific binding assay technique.

In the parent application it was described a new method and reagent means for assaying a liquid medium fo a ligand. The said method involved the utilization of a metal-labelled constituent comprising a conjugate of a metal-labelling substance and a binding component, the metal constituent being subsequently determined. The metal-labelled constituents were selected from various metal organo derivatives or metal coordination complexes represented by the general formula $M_m L_n^1 L_o^2 L_p^3 L_q^4 L_r^5 L_s^6$ wherein M is said metal atom, $L^1$ through $L_6$ are ligands or specific binding analogs thereof, which may be the same or different, m is an integer between 1 and 10, and n,o,p, q,r and s are integers between 0 and 12 provided that their sum does not exceed the coordination number of $M_m$.

The new method in the said parent application provided an elegant solution and overcame the known disadvantages of the prior art methods. Thus the new method avoids the utilization of radioactive materials required in the Radioimmunoassay, eliminates the expensive equipment required in the Free Radical Assay Technique and competes very favourable with the relatively expensive reagents required in the Enzyme Multiplied Immunoassay Technique. It was found that this new method is very accurate and sensitive being at the same time easily applicable in any laboratory without requiring skilled persons or expensive equipment.

It is an object of the present invention to provide a test pack kit for use in assaying a liquid medium for a ligand. It is another object of the present invention to provide a test pack kit comprising a special designed assay tube which enables an easy and accurate determination of small quantities of chemical compounds in man, animals and plants. The invention consists in a test pack kit for use in assaying a liquid medium for a ligand which comprises in a packaged combination:

(a) at least two assay tubes, each tube having a cylindrical side arm which can be interconnected with the side arm of another assay tube to form a leak-proof connecting channel;
(b) an antiserum;
(c) a conjugate of a metal-labelling substance with said ligand;
(d) a separation agent in vials containing material used for separating the bound antibody-metal labelling complex from the unbound metal labelling substance;
(e) assay calibration standards-in vials containing known concentrations of unlabelled ligand, and
(f) instrument calibration standards-in vials containing several concentrations of the metal-labelling substance.

BRIEF DESCRIPTION OF THE DRAWING

The Drawing shows a cross-sectional view of the assay tube of the invention.

DETAILED DESCRIPTION OF THE INVENTION

The test pack kit can also contain assay buffer in vials containing a concentrated solution or mixture of solid buffer reagents to be diluted with or dissolved in distilled water. The antiserum can be in the form of a freeze-dried cake, in appropriate concentration or bound to the test-tube walls by adsorption or covalently bound. Also the assay calibrator standards can be in the form of a freeze-dried cake or concentrated solution to be dissolved in or diluted with assay buffer. In FIG. 1 attached to the present specification a preferred illustration of the assay tube is given. According to this preferred embodiment the cylindrical side-arm of one tube is inserted into the side-arm of another assay tube in order to form the leak-proof connecting channel having a length (h) and diameter (j). This arrangement allows for easy and complete transfers of liquids and solution located at the bottom (a) of one tube to another through said channel (h). The total length of each assay tube is (a+b) in which b is not less than a and preferable longer than a. To the assay tube is connected a stop-cock (d) which has an inner diameter (e) which enters into the assay tube with the diameter (c). Of course the diameters e and c are so selected as to form a leak-proof tube. In according to a most preferred embodiment the two test tubes which should be interconnected, are of differently coloured material which helps greatly in avoiding mix-up errors in the addition of the appropriate reagents and will be in particular helpful for an unskilled person to follow up the correct sequence in the required steps of the assay procedure. The special and novel feature of the assay tube according to this invention provides a closed system containing all the assay reagents in which the errors caused by pipetting or transfer of reagent components from one container to another, are reduced to a minimum. This requirement is particularly important in work with trace amounts of metal compounds. Another important advantage is that it is possible to obtain the free fraction and/or the bound fraction completely in two separate test tubes without any pipetting step. Thus, the effect of the separation agent on the results is minimized because interference with the equilibrium state of the immunological reaction is eliminated. As mentioned in the parent application, a basic requirement of the new immunoassay method refers to the metallohaptens. In the parent specification a detailed explanation on metallohapten structure and metal organo derivatives as well as principles of their general methods of preparation were presented. The organic moiety can be practically any organic compound provided that it contains a suitable functional group with which one can form a bond to the metal atom. The metal organo-derivative can be either an organo-metallic compound or a metal coordination complex. The more interesting organometallic compounds suitable for the present invention are those in which there is a direct covalent bond or a pi-bond. An illustration of a covalent bond is for instance mercury-carbon bond. Another example utilizing a pi-type bonding, is an organic moiety which includes a grouping such as allyl chloride or allyl alcohol. By reacting such an allyl alcohol with metal atoms such as palladium or nickel or platinum, a pi-allyl nickel, a pi-allyl palladium, or pi-allyl platinum compounds are formed whereby there is a relative strong chemical bond between the metal atom and the allyl electronic system of the organic moiety. Such a compound could then again be used as the metallo-hapten for the specific binding assay.

One of the advantages of the new method according to the parent application and also utilized in this continuation in part application, is the easy analysis of a compound through the determination of the metal component. Various easy methods are known and available for a metal determination such as emission, absorption and fluorescence spectrometry, various electrochemical methods and neutron activation. In particular commonly used is the atomic absorption determination of metals which is now recognized as a very sensitive and accurate method, a fact which attests to the versatility of the present invention even for the determination of very small amounts of unknown compounds in a broad range of applications.

The metal-labelled constituents were selected from various metal organo derivatives or metal coordination complexes represented by the general formula $M_m L_n^1 L_o^2 L_p^3 L_q^4 L_r^5 L_s^6$ wherein M is said metal atom, $L^1$ through $L^6$ are ligands or specific binding analogs thereof, which may be the same or different, m is an integer between 1 and 10, and n,o,q,r and s are integers between 0 and 12 provided that their sum does not excaed the coordination number of $M_m$.

The metal may be any metal element or combination of metal elements and preferably metal elements selected from the transition metals of group IB, IIB, IIIB, IVB, VB, VIB, VIIB and VIII of the Periodic Table of elements. Particularly useful are the so-called noble metals from group VIII such as Ru, Rh, Pd, Ir and Pt. For example the element Platinum occupies a special position in the organo-metal complex chemistry due to the variety of compounds which this element can form. Due to the fact that Pt can exist in many oxidation states from 0 to +4, the number of platinum organo-compounds is very high so that any desired complex can be envisaged and reduced to practice. Other elements which have metal-like properties, such as As, B, Sb, Se, Si, Sn, Te, Ge, as well as the lanthanides elements could be used to prepare metallo-haptens.

Hereinafter will be described the sequency of the steps involved in the assay procedure for the determination of a ligand with the test pack kit according to the present invention.

1. Before the start of the assay each of the instrument calibration standards M are diluted with 1 ml assay buffer and the metal content is determined by the appropriate analytical method to establish a calibration curve of metal concentration versus analytical instrument signal.
2. Label the provided assay tubes A,B,C,D,E for assay calibration standards and sufficient additional tubes for the unknown analyte samples. Use the same label for both Parts I and II (I and II designating the pair of assay tubes which have to be interconnected) of each assay-tube assembly.
3. Add 400 $\mu l$ of reconstituted assay buffer to each of Part II of the assay tube assembly containing the metalloantigen tracer.
4. Add 50 $\mu l$ of each reconstituted calibration standard to Part II of assay tube assembly labelled A-E and 50 $\mu l$ of unknown analyte samples to Part II of other assay tubes and mix well each assay tube.
5. Transfer completely the contents of Part II of the assay tube assembly to Part I through the connection tube linking Part I to Part II, allow to stand for 10 minutes and mix gently for about 1–3 minutes.
6. Incubate assay tubes for appropriate period (30 minutes or more).
7. Add 100 $\mu l$ of the separation agent to Part I of the assay tube assembly, mix well and incubate for 30 minutes. (This step is omitted if the antibody reagent is bound to the walls of the assay tube by adsorption or by a covalent bond).
8. Disconnect Part I from Part II of each assay-tube assembly and centrifuge Part I of each of the assay tubes assembly at 1600–2500 G. (This step is omitted if the antibody reagent is bound to the walls of the assay tube by adsorption or by covalent bond). With suitable centrifuge heads, the whole test tube assembly may be centrifuged without having to disconnect Parts I and II.
9. After centrifugation reconnect Part I of each assay-tube assembly to its Part II pair (same assay labelled pair) and transfer the supernatant eluent from Part I into Part II. This separates the "bound" from the "free" and prevents disturbance of the equilibrium.
10. Analyze for metal content in the supernatant solution (or the precipitate) of each assay tube by appropriate analytical methods. For example, inject 20–30 $\mu l$ portions of (or more if necessary) supernatant solution (or precipitate) in the flame or flameless unit of an atomic absorption spectrophotometer and determine the amount of metal present in each sample, with the help of the calibration curve determined in step 1 above.
11. Plot the given known concentrations of the analyte in calibration standards S (assay tubes A-E) and the metal concentrations found in Step 10, on graph paper (logit-log or semi-log paper) and draw the best fit line.
12. Use the calibration curve obtained in Step 11 above the determine the concentration of unknown analyte from the metal-content data obtained in step 10 above.

While the invention has been described in connection with specific embodiments thereof, it will be understood that it is capable of further modifications, and this patent is intended to cover any variation, uses or adaptations of the invention and including a such departures from the present disclosure as come within known or customary practicle in the art to which the invention pertains and as may be applied to the essential features hereinbefore set forth and as fall within the scope of the invention.

I claim:

1. A test pack kit for use in assaying a liquid medium for a ligand which comprises in a packaged combination:
   (a) at least two assay tubes, each tube having a cylindrical side arm which can be interconnected with the side arm of another assay tube to form a leak-proof connecting channel;
   (b) an antiserum;
   (c) a conjugate of a metal-labelling substance with said ligand;
   (d) a separation agent in vials containing material used for separating the bound antibody-metal labelling complex from the unbound metal labelling substance;

(e) assay calibration standards-in vials containing known concentrations of unlabelled ligand, and (f) instrument calibration standards-in vials containing several containing several known concentrations of the metal-labelling substance.

2. A test pack kit according to claim 1, wherein the test pack kit contains assay buffer.

3. A test pack kit according to claim 1, wherein the pair assay tubes to be interconnected are made of differently coloured material.

4. A test pack kit according to claim 1, wherein the antiserum is in the form of a freeze dried cake in appropriate concentration.

5. A test pack kit according to claim 1, wherein the antiserum is bound to the assay-tube walls by absorption or covalently bound.

6. A test pack kit as in claim 1, wherein said metal-labelled conjugate comprises said ligand or a specific binding analog thereof bound to a metal organo-derivative.

7. A test pack kit as in claim 1, wherein said metal organo-derivative is represented by the general formula $$M_m L_n^1 L_o^2 L_p^3 L_q^4 L_r^5 L_s^6$$

wherein M is said metal atom, $L^1$ through $L^6$ are ligands or specific binding analogs thereof, which may be the same or different, m is an integer between 1 and 10, and n, o, p, q, r and s are integers between 0 and 12 provided that their sum does not exceed the coordination number of $M_m$.

8. A test pack kit as in claim 1, wherein said metal organo-derivative is an organo-metallic compound or a metal coordination complex.

9. A test pack kit as in claim 8, wherein said organo-metallic compound is characterized by covalent bonding.

10. A test pack kit as in claim 8, wherein said organo-metallic compound is characterized by pi-bonding.

11. A test pack kit as in claim 1, wherein said specific binding partner of said ligand is in an insoluble form.

12. A test pack kit as in claim 1, which additionally comprises a container of an antibody to said specific binding partner of said ligand, which antibody is in an insoluble form.

13. A test pack kit as in claim 1, wherein the metal-labelling substance is a transition metal selected from the group consisting of I B, II B, III B, IV B, V B, VI B, VII B, and VIII of the Periodic Table of elements.

14. A test pack kit as in claim 13, wherein said metal is selected from the group consisting of Fe, Hg, Cr, Co, Pd, Au, Mn and Cu.

* * * * *